United States Patent [19]

Lazarof

[11] Patent Number: 5,681,167
[45] Date of Patent: Oct. 28, 1997

[54] DENTAL ASSEMBLY AND PROCESS FOR PREPARING A TOOTH PROSTHESIS

[76] Inventor: Sargon Lazarof, 21237 Mulholland Dr., Woodland Hills, Calif. 91364

[21] Appl. No.: 590,275

[22] Filed: Jan. 5, 1996

[51] Int. Cl.$^6$ ............................................... A61C 8/00
[52] U.S. Cl. ............................................ 433/174; 433/173
[58] Field of Search .................................. 433/172, 173, 433/174, 175, 169, 177; 606/73

[56] References Cited

U.S. PATENT DOCUMENTS

| | | |
|---|---|---|
| 3,708,883 | 1/1973 | Flander ................................. 433/174 |
| 4,011,602 | 3/1977 | Rybicki et al. ....................... 433/173 |
| 4,850,870 | 7/1989 | Lazzara et al. ...................... 433/173 |
| 5,004,421 | 4/1991 | Lazarof . |
| 5,022,860 | 6/1991 | Lazzara et al. ...................... 433/174 |
| 5,087,199 | 2/1992 | Lazarof . |
| 5,344,457 | 9/1994 | Pilliar et al. ......................... 433/174 |
| 5,470,230 | 11/1995 | Daftary et al. . |
| 5,489,210 | 2/1996 | Hanosh ................................. 433/173 |
| 5,513,989 | 5/1996 | Crisio .................................. 433/173 |
| 5,564,921 | 10/1996 | Marlin ................................. 433/173 |
| 5,564,924 | 10/1996 | Kwan .................................. 433/173 |

*Primary Examiner*—John J. Wilson
*Assistant Examiner*—Ralph A. Lewis
*Attorney, Agent, or Firm*—Kelly Bauersfeld Lowry & Kelley, LLP

[57] ABSTRACT

A dental assembly includes an implant having a tubular body portion which can be positively secured within a bore in a jawbone by an expander mechanism, and a two-piece abutment secured to the implant and having a collar which is incapable of rotation with respect thereto. In a related process for preparing a tooth prosthesis, a transfer sleeve is utilized in a process to replicate conditions in the mouth, including the configuration of the abutment assembly, in manufacturing a custom analog. A custom analog is cast into a stone mold to provide an exact duplicate of the mouth. From this stone mold a crown can be manufactured in a laboratory to precisely fit in the user's mouth over a customized abutment. A treatment crown sleeve may be utilized in connection with a provisional tooth.

37 Claims, 15 Drawing Sheets

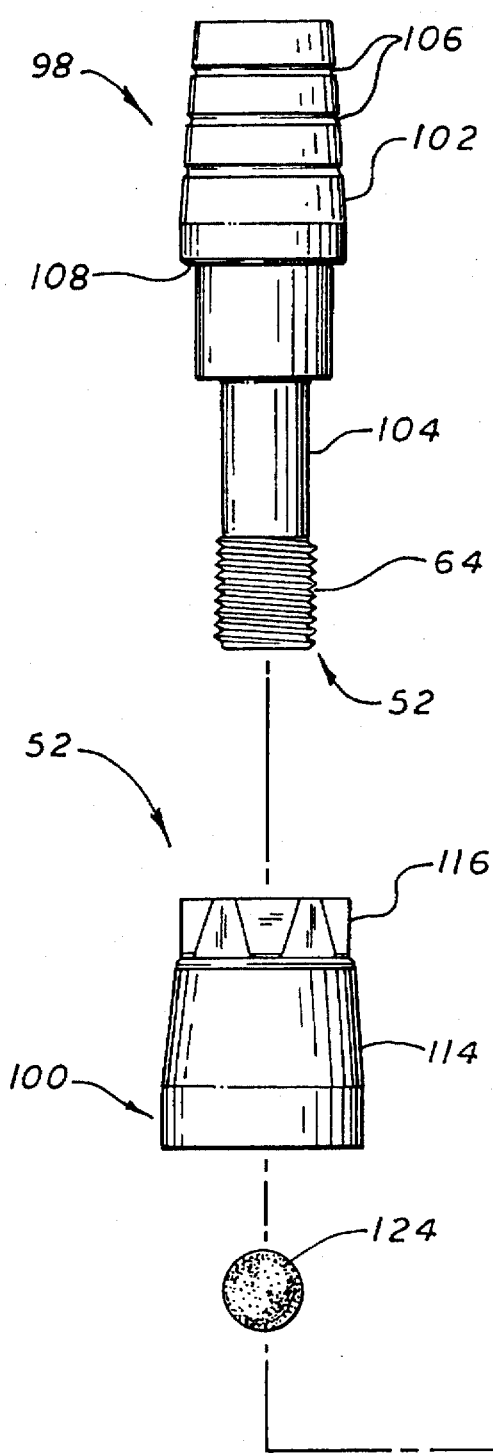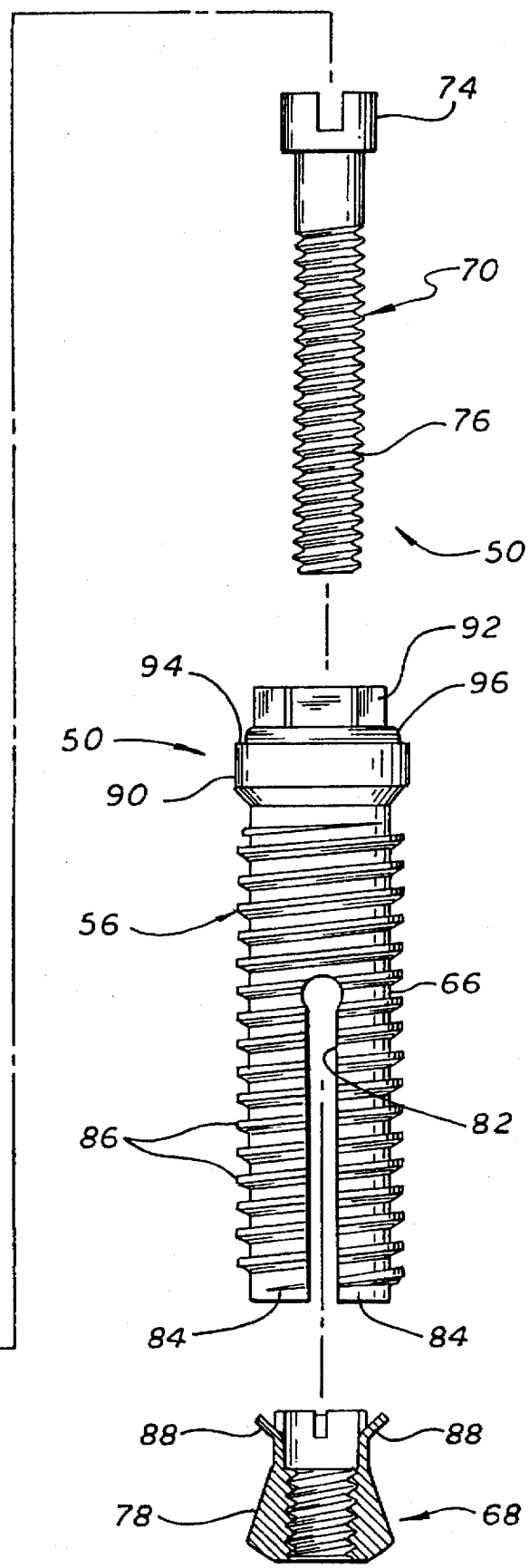
FIG. 2

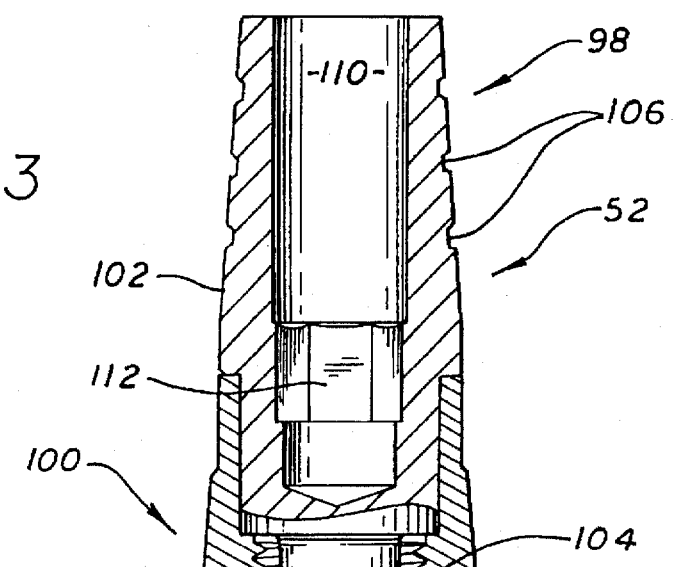
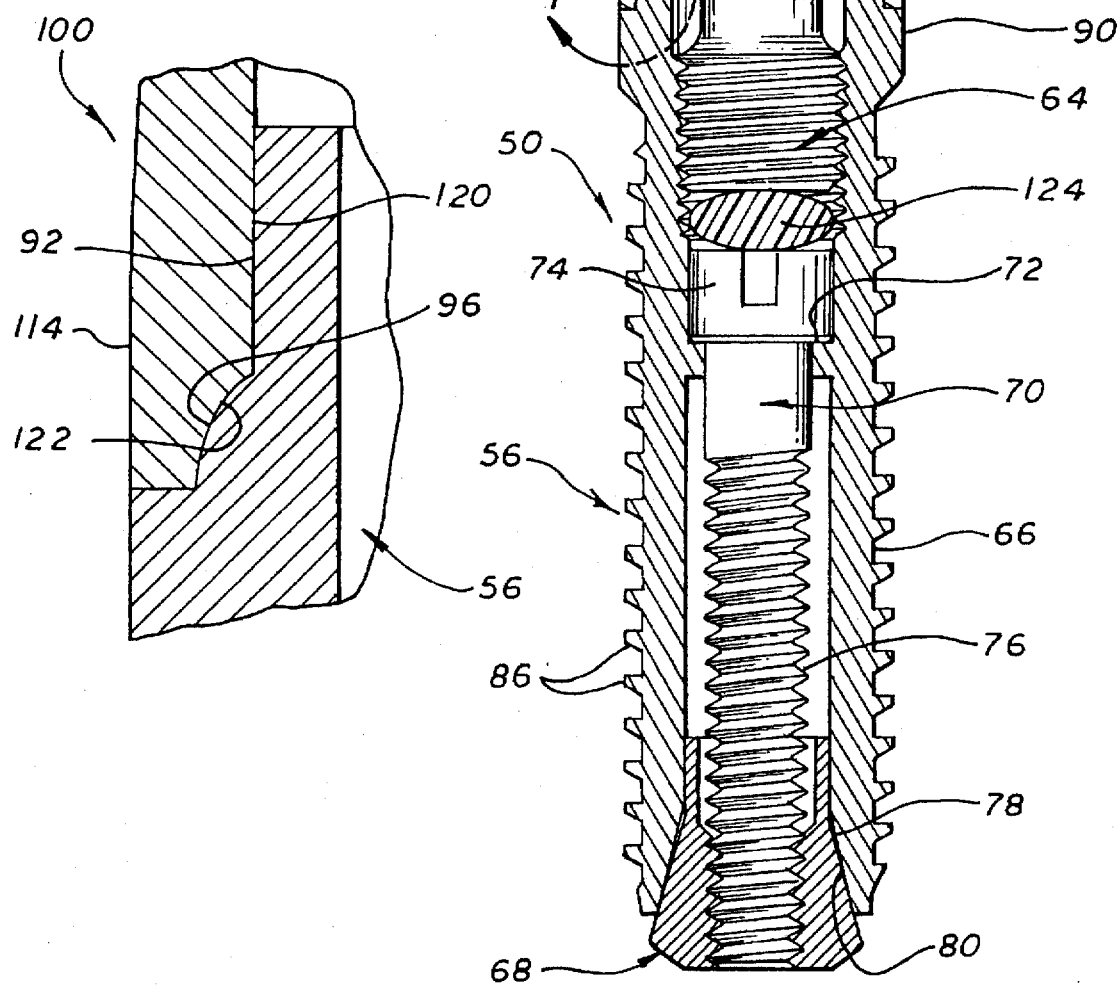
FIG. 3
FIG. 4

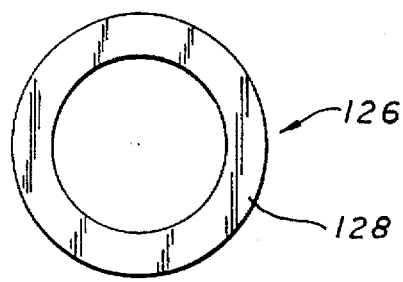
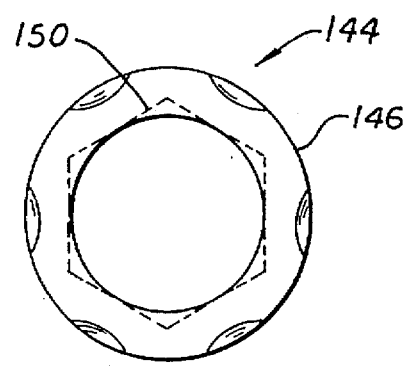
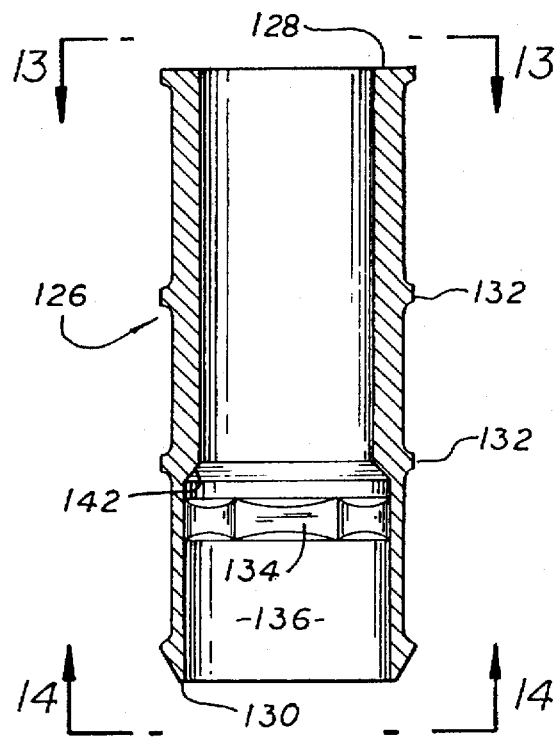
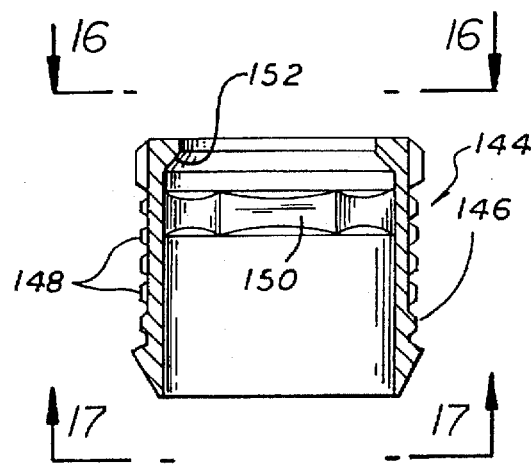
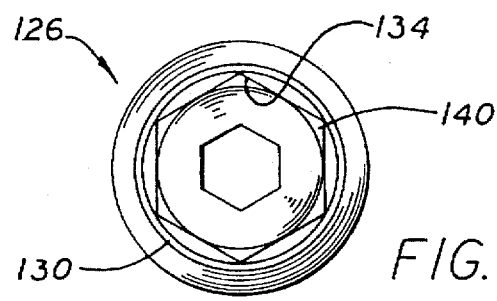
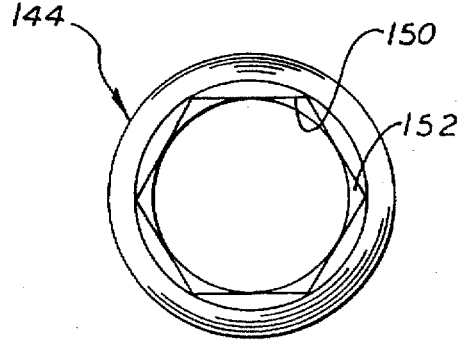

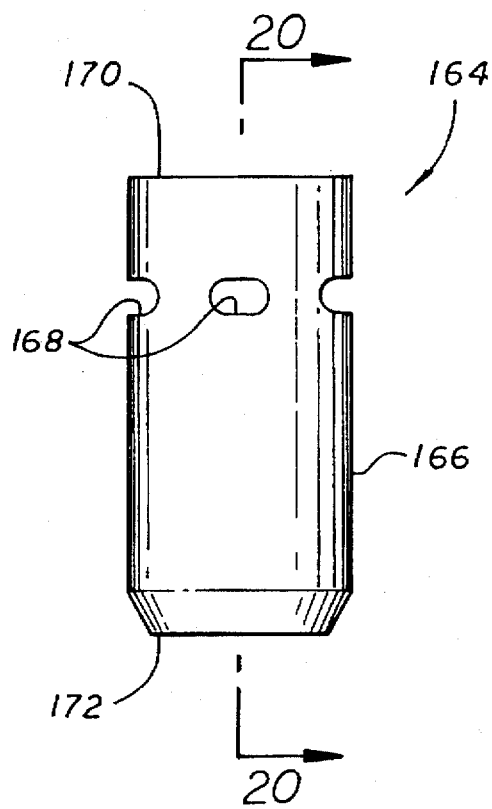
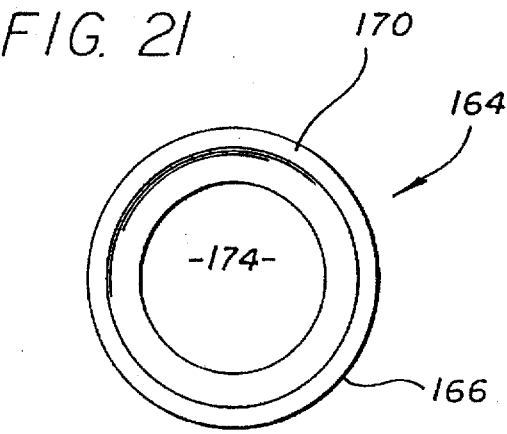
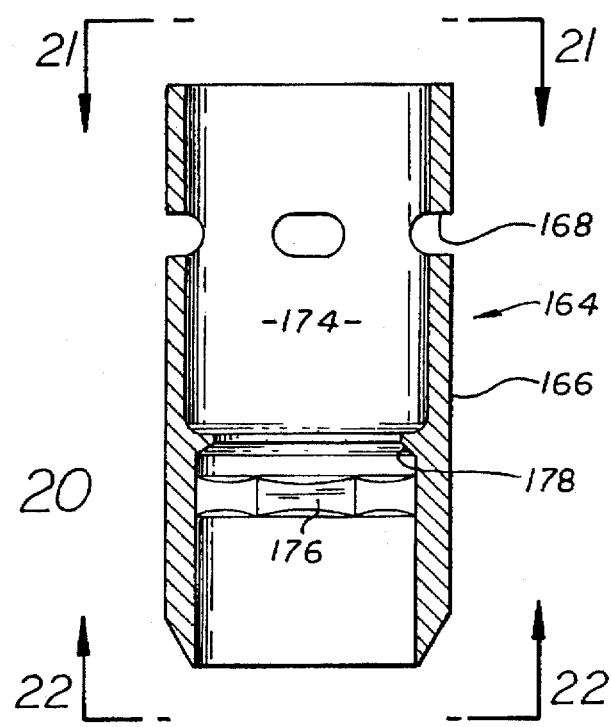
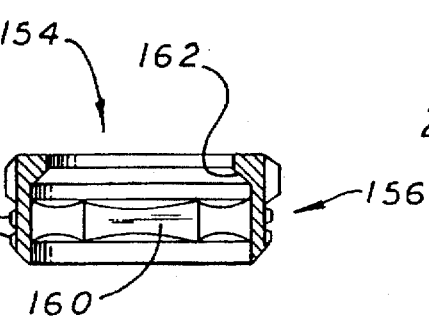
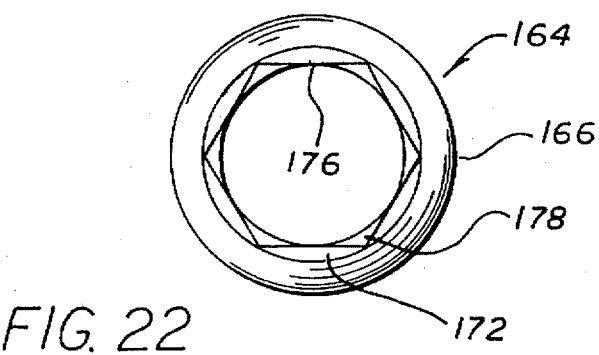

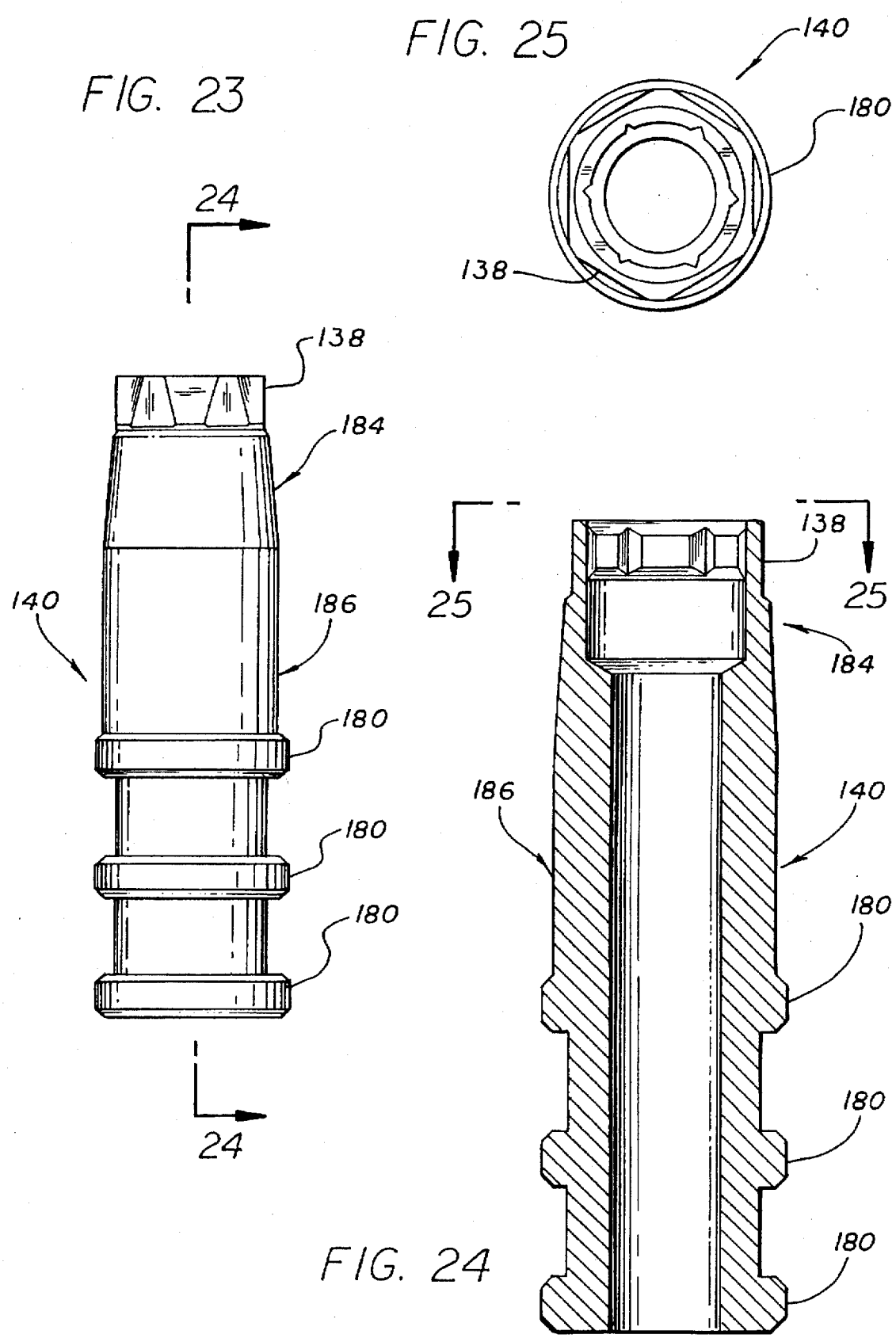

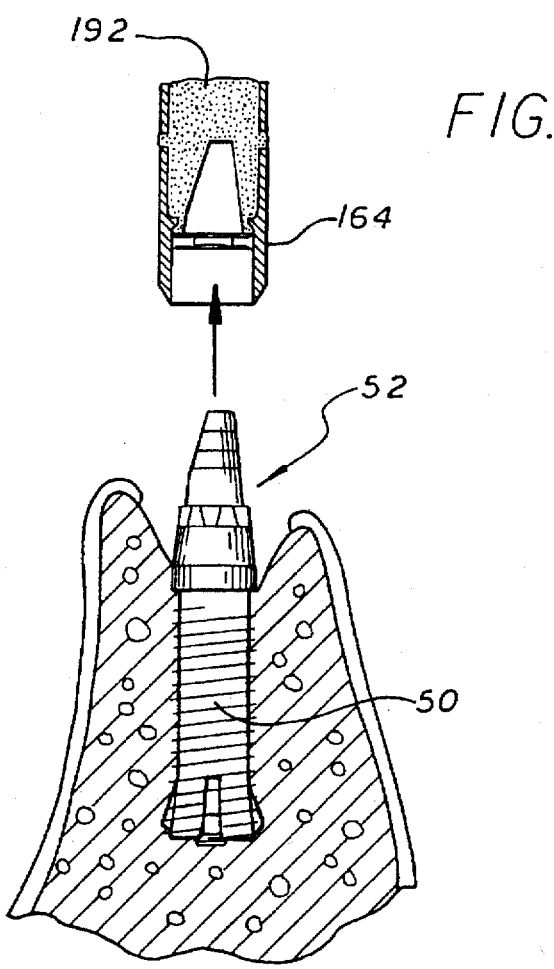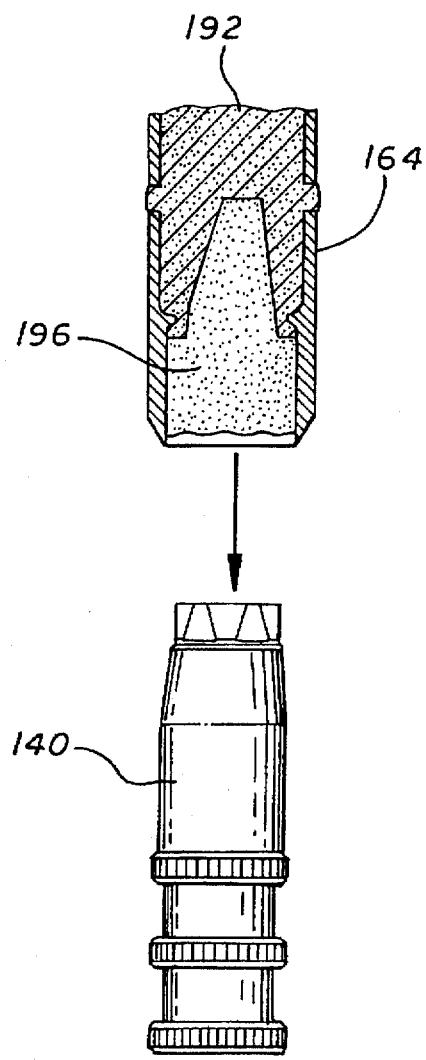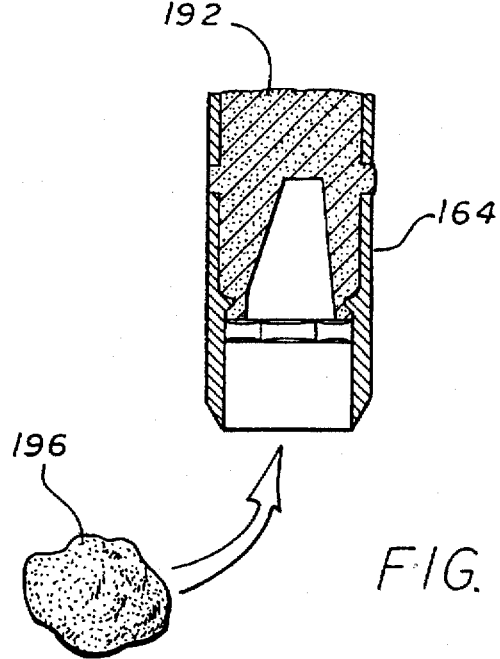
FIG. 32
FIG. 34
FIG. 33

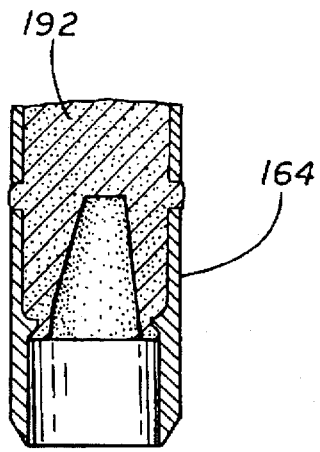
FIG. 37
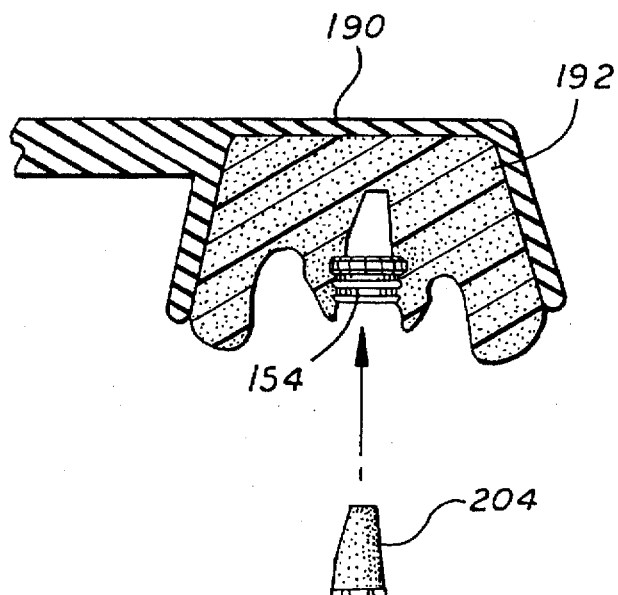
FIG. 38
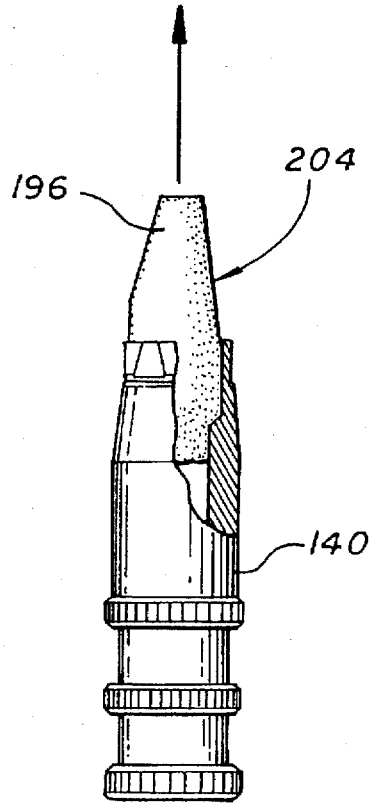
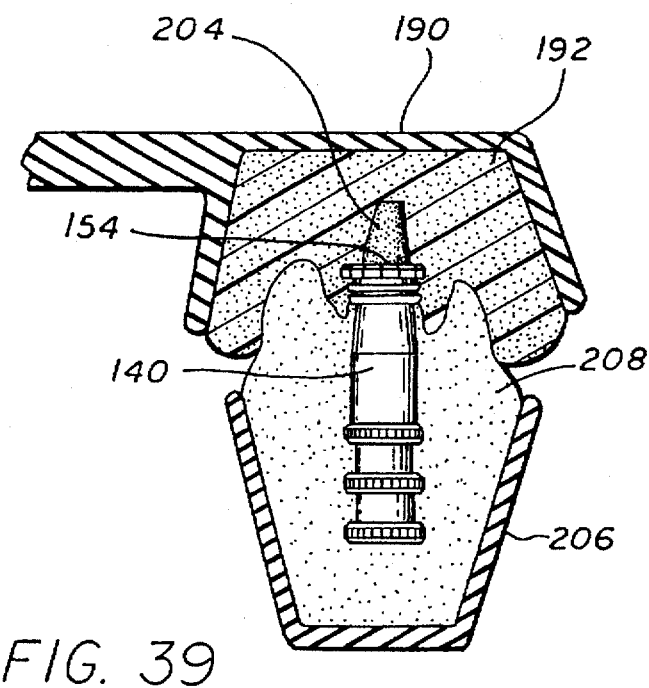
FIG. 39

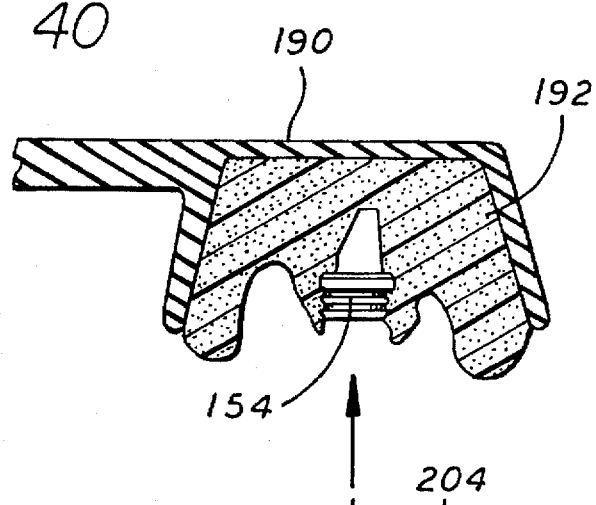
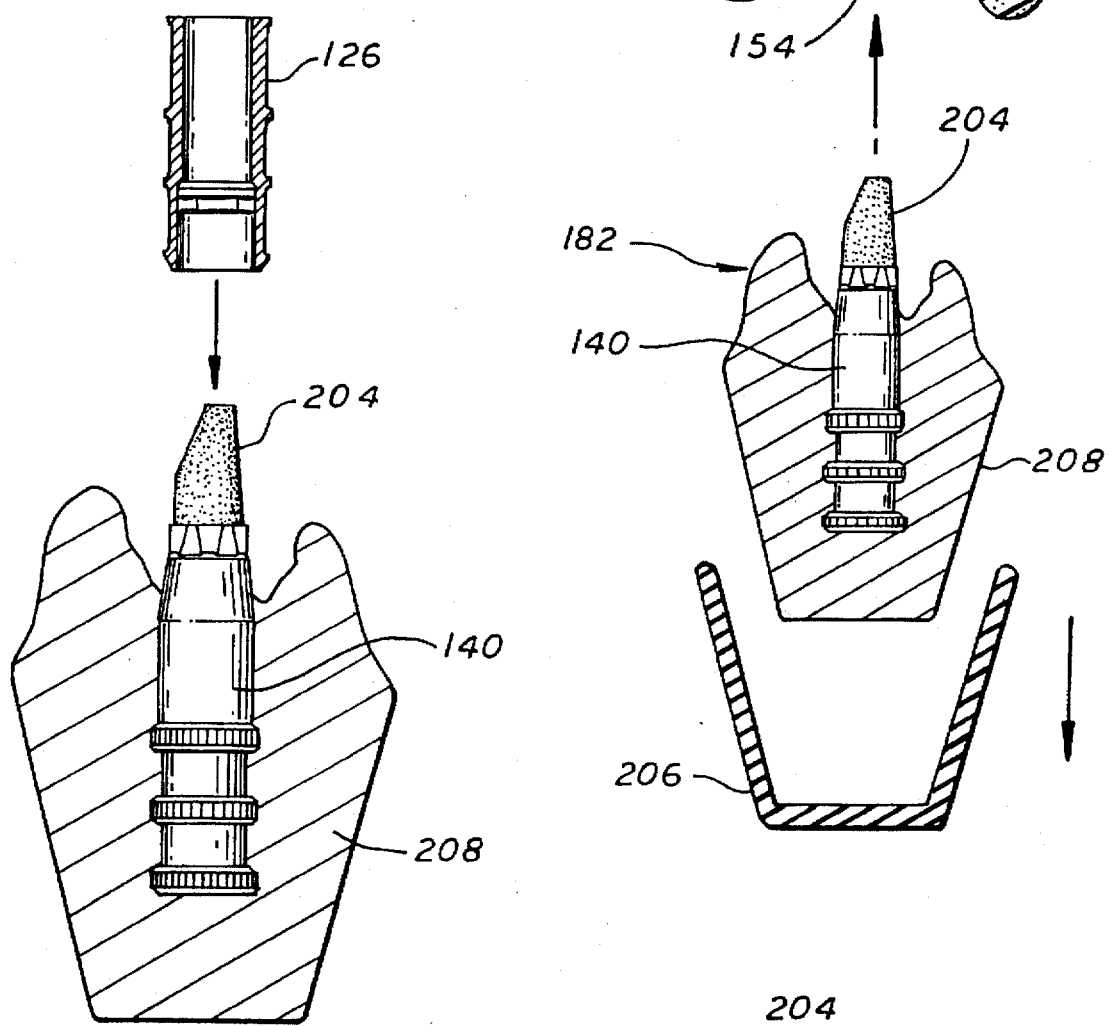
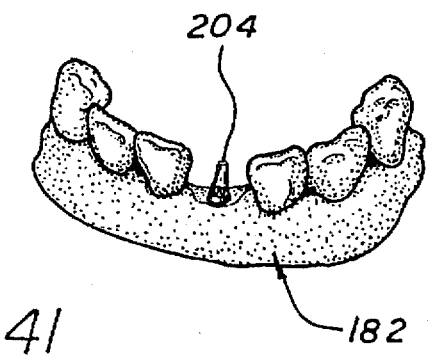

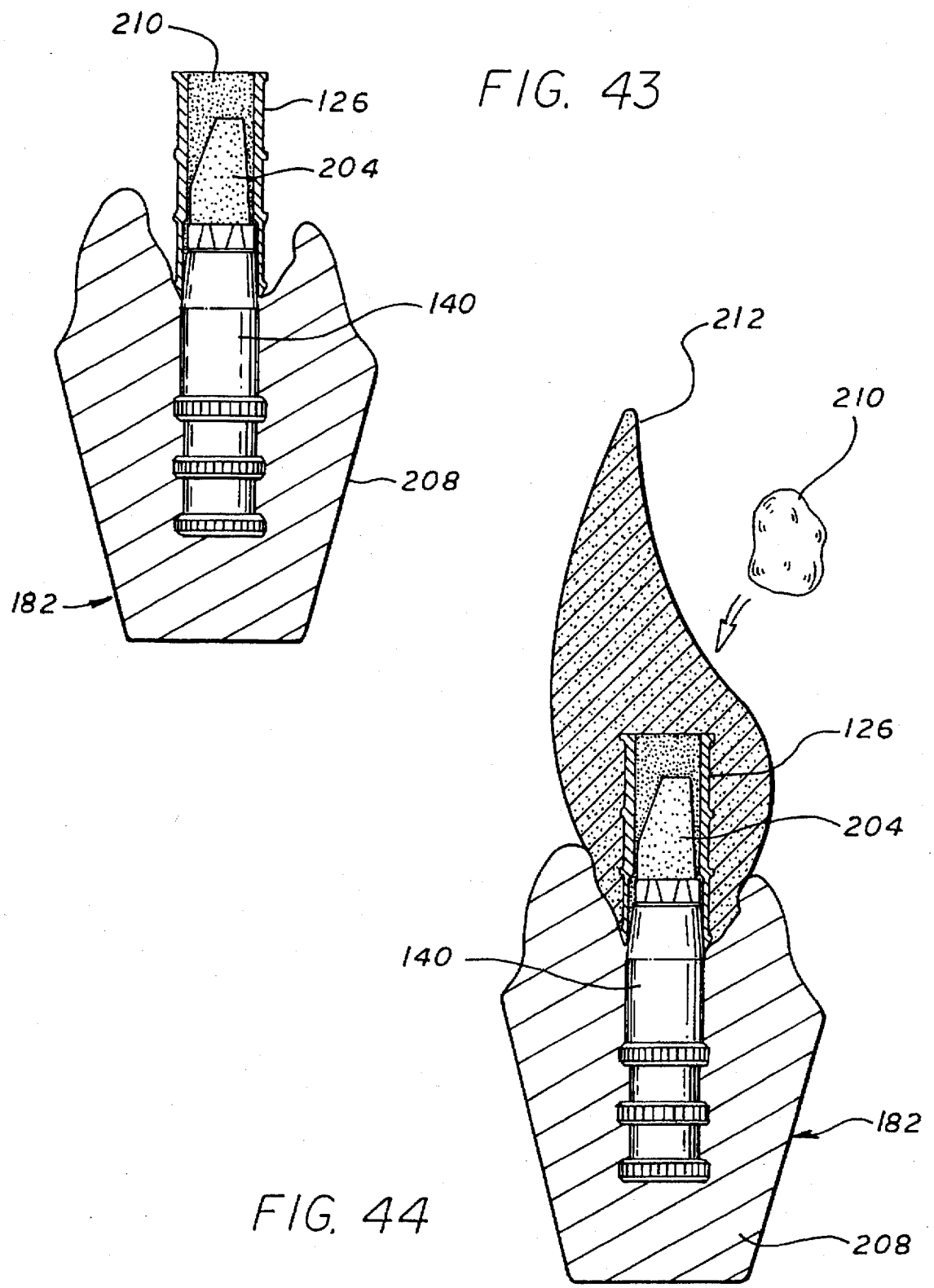

DENTAL ASSEMBLY AND PROCESS FOR PREPARING A TOOTH PROSTHESIS

BACKGROUND OF THE INVENTION

The present invention relates generally to dental implants and processes for preparing tooth prostheses. More particularly, the present invention concerns a dental implant which includes a tubular body portion that can be positively secured within a bore in a jawbone by an expander mechanism, a two-piece immediate fixed abutment for use in connection with the dental implant, and a unique transfer technique for preparing a tooth prosthesis.

Dental implants of the character receivable within a bore provided in the jawbone are old in the art. Typically such implants comprise an apertured body portion which is emplaced within a bore drilled in the bone. The body portion is designed so that during a period of about four to six months after its emplacement within the bore, bone tissue will grow into the aperture so as to secure the body portion of the implant in place within the bone bore. Following this four to six month period, an artificial tooth or other prosthetic component is secured to the body portion.

The procedure is undesirable in several respects. In the first place, the procedure is protracted and requires multiple visits to the oral surgeon. Secondly, during the extended period of time required for the bone tissue to grow into and around the implant, the patient is left with an uncomfortable and unsightly cavity where the prosthetic component, such as an artificial tooth, will eventually go. Additionally, this procedure does not always provide adequate anchoring of the implant to the jawbone so that in time the implant can loosen.

In order to overcome the drawbacks of the standard procedure described above, several types of implants using mechanical locking means for securing the implant in place within the bore in the jawbone have been suggested. Exemplary of such devices is the device described in U.S. Pat. No. 3,708,883 issued to Flander. An improved dental implant is illustrated and described in U.S. Pat. Nos. 5,004,421 and 5,807,199 issued to Lazarof. The Lazarof dental implant makes use of mechanical securement means, but unlike the Flander device, the Lazarof device includes means by which selected dental prosthetics of standard design can be threadably interconnected. In this way, angular corrections of the prosthetic, such as an artificial tooth, can readily be made. Further, in one form, the Lazarof implant is positively secured within the bore in the bone by two separate but cooperating securement mechanisms. The first securement mechanism comprises self-tapping, external threads provided on the tubular body of the device which are threaded into the bone by rotating the device in a first direction. The second cooperating securement mechanism comprises a plurality of bone penetrating anchor blades formed on the skirt portion of the tubular body which are moved into a bone engagement position only after the implant has been securely threaded into the bone. The anchor blades are moved into the bone engagement configuration by rotating a threaded expander member also in a first direction. However, because the threads on the expander member are opposite to the threads on the tubular body, rotational forces exerted on the expander member continuously urge the implant in a tightening direction. In other words, as the anchor blades are urged outwardly, the implant is continuously urged into threaded engagement with the bone. This double locking approach permits the selected prosthetic component to be connected to the implant immediately without the patient having to return to the oral surgeon a second time.

Often an abutment over which a tooth prosthesis is formed, is fixed to an exposed end of the dental implant. Typically, the prior abutments either accommodated a bolt which passed longitudinally through an open central bore for securing the abutment to the implant, or were provided an integral threaded shaft to permit the abutment to be screwed directly into the implant. Such abutment to implant attachment has, however, not been entirely satisfactory since it is very undesirable that any relative movement between the abutment and the implant be permitted once brought together, and particularly after a prosthesis has been attached to the abutment. Without actually cementing the abutment to the implant, there always exists the possibility that the abutment will loosen therefrom, resulting in undesirable rotation of the dental prosthesis.

Since dental prosthetic devices are typically manufactured in a laboratory, a major concern of dentists and laboratory technicians is the accurate transfer of information from the patient/dentist to the lab. Such information includes the size and shape of adjacent teeth, the position of the implant and the precise configuration of the abutment, since it is often shaped by the dentist in preparation.

Accordingly, there has been a need for an improved dental implant which is of simplified construction and which incorporates advantages over the prior art. Further, there exists a need for an improved immediate fixed abutment which is incapable of rotation relative to the dental implant once a dental prosthesis, such as a crown, is applied thereto. Moreover, a novel process for preparing a tooth prosthesis is needed which permits a dentist and laboratory to accurately replicate conditions existing within the patient's mouth, to facilitate crown preparation in the laboratory. The present invention fulfills these needs and provides other related advantages.

SUMMARY OF THE INVENTION

The present invention resides in a novel dental assembly including a dental implant and a two-piece abutment assembly which is attachable to the dental implant. More particularly, the dental implant includes a skirt receivable within a bore provided in a jawbone of a patient, and supporting means adjacent to the skirt and extending outwardly from the bore. The supporting means includes at least one radially outwardly facing planar surface. The abutment assembly includes an abutment collar having at least one radially inwardly facing planar surface which, when the abutment collar is positioned over at least a portion of the supporting means, the radially facing surfaces of the supporting means and the abutment collar interfit to prevent rotation of the abutment collar relative to the dental implant. The abutment assembly further includes an abutment screw having a head positionable in abutting relation to the abutment collar opposite to the dental implant, and a shank extendable through the abutment collar for connection to the dental implant. The present invention further resides in a novel and related process for preparing a tooth prosthesis for attachment to the abutment assembly.

In a preferred form of the invention, the dental implant comprises an elongated hollow body including a skirt receivable within the bore provided in the jawbone of the patient, and means adjacent to the skirt and extending outwardly from the bore for supporting a prosthetic component (in the present invention, the abutment assembly). The skirt is radially movable within the bore from a first retracted position to a second expanded position and includes an internal shoulder. The supporting means includes at least one radially outwardly facing planar surface that may be engaged by the prosthetic component to prevent relative rotation therebetween. The dental implant further includes a draw screw which includes a head that rests on the internal shoulder of the hollow body, and a threaded shank which extends to an end of the skirt. An expansion nut having a frustoconically-shaped skirt-engaging side wall includes an inner threaded cavity into which the shank of the draw screw is threaded. Rotation of the draw screw through the inner cavity of the expansion nut causes radial movement of the skirt from the first retracted position to the second expanded position.

The skirt comprises at least two anchor segments movable from the first retracted position to the second expanded position. The skirt further includes an inclined internal surface, and a plurality of circumferentially spaced, longitudinally extending slits which separate the anchor segments. The anchor segments include bone penetrating means for penetrating the bone of the patient upon movement of the segments into the second expanded position.

The expansion nut comprises a skirt engaging portion which has an inclined external surface moveable into engagement with the inclined internal surface of the skirt upon rotation of the draw screw through the inner cavity of the expansion nut. The expansion nut further includes a plurality of tabs configured for alignment with the longitudinally extending slits. The draw screw is positioned entirely within the skirt and is accessible through the supporting means.

The supporting means includes a ring having a diameter larger than the bore. The ring provides a shoulder facing away from the bore. The supporting means further includes an upper hexed portion extending away from the ring which presents a plurality of radially outwardly facing planar surfaces. A bevel is further provided adjacent to the shoulder which surrounds the upper hexed portion.

An elastomeric ball is compressed between the abutment screw shank and the draw screw head.

The abutment collar includes a plurality of radially inwardly facing planar surfaces which form a hexed inner peripheral surface. When the abutment collar is positioned over at least a portion of the supporting means, the radially facing surfaces of the supporting means and the abutment collar interfit to prevent rotation of the abutment collar relative to the hollow body. The abutment collar includes a main body positionable over at least a portion of the supporting means, and a collar opposite the implant assembly relative to the main body. The collar includes a plurality of radially outwardly facing planar surfaces which form a hexed outer periphery. The abutment collar further includes an internal threaded section through which the abutment screw shank extends. An inner bevel is configured to engage a complementary outer bevel provided on the dental implant. Preferably, the abutment collar is plated with titanium nitride to give it a gold color.

The abutment screw includes a head positionable in abutting relation to the abutment collar opposite the hollow body. The shank is extendable through the abutment collar for connection to the hollow body. In this regard, the shank is threaded at an end thereof and is received within internal threads of the hollow body.

In accordance with the process for preparing a tooth prosthesis for attachment to the abutment assembly, a transfer sleeve is first placed over the abutment and then an impression is taken of the mouth, wherein the transfer sleeve is transferred to the impression. An impression sleeve is then utilized to take an impression of the abutment. The impression of the abutment in the impression sleeve is then filled with a composite material. The impression sleeve is then seated on an implant analog. After the composite material has set, the impression sleeve and its impression material are removed from the implant analog to produce a custom analog which is an exact duplicate of the abutment.

The custom analog is then placed into the impression of the mouth through the transfer sleeve. A stone mold is created of the mouth utilizing the impression of the mouth having the mounted custom analog therein, and the stone mold is then utilized to form the tooth prosthesis.

More particularly, a waxing sleeve is placed over the custom analog protruding from the stone mold. The waxing sleeve is filled with wax and a wax-up of the dental prosthesis is then built over the waxing sleeve. The wax-up and the waxing sleeve are then removed from the stone mold and invested in another stone mold which is then cast to manufacture the tooth prosthesis in a known manner.

Preferably the transfer sleeve, the impression sleeve and the waxing sleeve all lock into place over respective components of the abutment and the custom analog in the same manner which prevents relative rotation therebetween. Once the crown is manufactured (to have an exterior shape corresponding to the wax-up and an interior cavity corresponding to the shape of the abutment assembly), an adhesive material is utilized to attach the dental prosthesis to the abutment assembly in the patient's mouth.

As an interim measure, a provisional may be manufactured for placement over the abutment assembly utilizing a treatment crown sleeve positioned within a denture tooth filled with a composite material. Preferably, the treatment crown sleeve, as well as the abutment collar, are plated with titanium nitride to give these components a gold appearance.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 2 is an exploded elevational and partially sectional view of the dental implant and abutment assembly of FIG. 1;

FIG. 3 is an elevational section of the components illustrated in FIG. 2, illustrating attachment of the abutment assembly to the dental implant;

FIG. 4 is an enlarged fragmented sectional view taken of the area generally illustrated by the number 4 in FIG. 3;

FIG. 12 is an elevational sectional view of a waxing sleeve, the use of which is more fully explained in connection with the discussion of FIGS. 42–45;

FIG. 13 is a top plan view of the waxing sleeve taken generally along the line 13—13 of FIG. 12;

FIG. 14 is a bottom plan view of the waxing sleeve taken generally along the line 14—14 of FIG. 12;

FIG. 15 is an elevational sectional view of a treatment crown sleeve, the use of which is more fully described in connection with the discussion of FIGS. 35 and 36;

FIG. 16 is a top plan view of the treatment crown sleeve taken generally along the line 16—16 of FIG. 15;

FIG. 17 is a bottom plan view of the treatment crown sleeve taken generally along the line 17—17 of FIG. 15;

FIG. 18 is an elevational sectional view of a transfer sleeve, the use of which is more fully described in connection with the discussion of FIGS. 28–30 and 38–40;

FIG. 19 is an elevational view of an impression sleeve which will be more fully described in connection with the discussion of FIGS. 31–34 and 37;

FIG. 20 is an enlarged elevational section of the impression sleeve taken generally along the line 20—20 of FIG. 19;

FIG. 21 is a top plan view of the impression sleeve taken generally along the line 21—21 of FIG. 20;

FIG. 22 is a bottom plan view of the impression sleeve taken generally along the line 22—22 of FIG. 20;

FIG. 23 is an elevational view of an implant analog whose use is discussed in connection with the description of FIGS. 34 and 37–45;

FIG. 24 is an enlarged sectional view taken generally along the line 24—24 of FIG. 23;

FIG. 25 is a top plan view of the implant analog taken generally along the line 25—25 of FIG. 24; and FIGS. 26–46 illustrate steps involved in a process for preparing a tooth prosthesis in accordance with the present invention, wherein:

FIG. 26 is a cross-sectional view of a jawbone illustrating the dental implant positioned therein;

FIG. 27 illustrates the steps of fastening the abutment assembly to the dental implant and shaping the same to form a custom abutment;

FIG. 28 illustrates the step of placing the transfer sleeve over the custom abutment;

FIG. 29 illustrates the step of taking an impression of the mouth over the custom abutment and the transfer sleeve;

FIG. 30 illustrates the step of removing the transfer sleeve with the impression material;

FIG. 31 illustrates the step of placing the impression sleeve filled with impression material over the custom abutment;

FIG. 32 illustrates the step of removing the impression sleeve from the mouth;

FIG. 33 illustrates the step of filling the cavity within the impression sleeve corresponding to the shape of the custom abutment with a composite material;

FIG. 34 illustrates the step of placing the composite-filled impression sleeve onto the implant analog;

FIG. 35 illustrates the step of placing the treatment crown sleeve of FIG. 15 over the custom abutment and filling a provisional (temporary tooth) with a composite material;

FIG. 36 illustrates placing the composite filled provisional over the custom analog and the treatment crown sleeve as an interim step to provide a temporary tooth prosthesis while the permanent crown is being manufactured in the laboratory;

FIG. 37 illustrates the step of removing the impression sleeve from the implant analog leaving a stone die corresponding in shape to the custom abutment assembly, thereby forming a custom analog;

FIG. 38 illustrates the step of inserting the custom analog into the transfer sleeve embedded in the impression of the mouth;

FIG. 39 illustrates the step of making a stone cast of the mouth over the custom analog;

FIG. 40 illustrates the step of removing the cast and the mouth impression from the stone mold;

FIG. 41 is a perspective view illustrating the stone mold having the custom analog embedded therein;

FIG. 42 illustrates the step of placing a waxing sleeve over the custom analog extending from the stone mold;

FIG. 43 illustrates the step of filling the waxing sleeve with a wax to surround the exposed portion of the custom analog;

FIG. 44 illustrates the step of forming a wax-up of the tooth prosthesis;

FIG. 45 illustrates the step of removing the wax-up for purposes of forming a crown utilizing standard casting procedures; and FIG. 46 illustrates the step of fixing the final crown having an internal cavity precisely matching the external configuration of the customized abutment assembly, to the customized abutment assembly within the patient's mouth.

DETAILED DESCRIPTION OF THE PREFERRED EMBODIMENT

Figure 1:
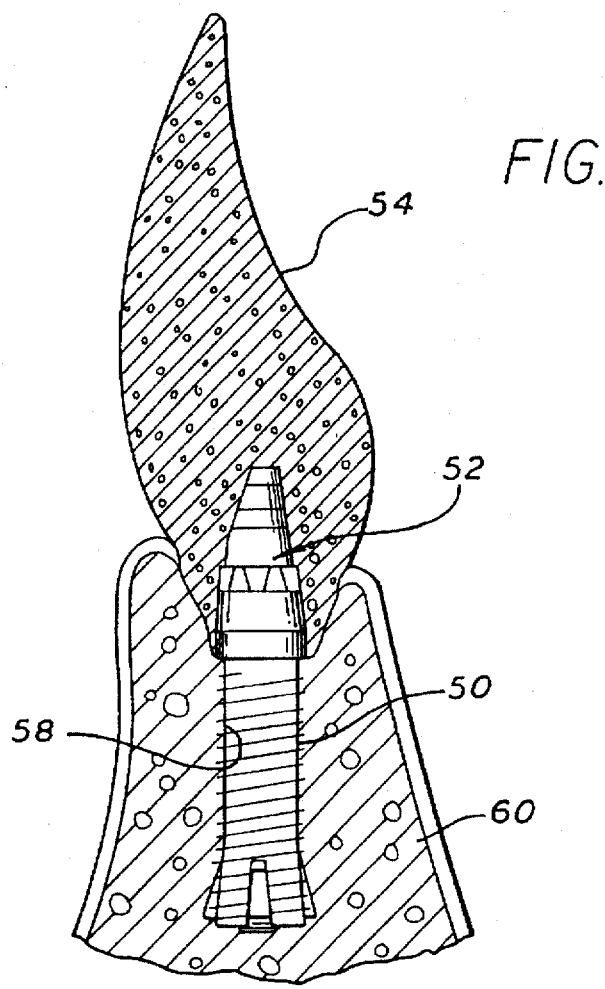
FIG. 1 is a partially fragmented sectional view illustrating a dental implant embedded within a jawbone, the implant supporting a customized abutment assembly to which a porcelain crown is attached.
Figure 6:
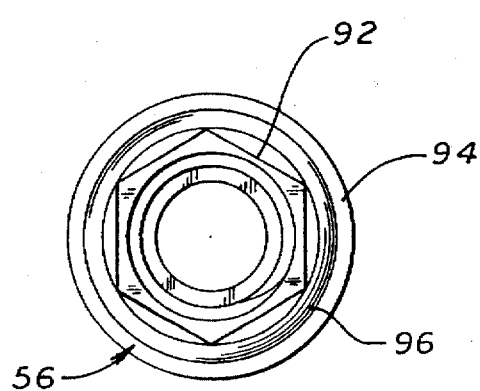
FIG. 6 is a top plan view of the tubular body portion taken generally along the line 6—6 of FIG. 5.

As shown in the drawings for purposes of illustration, the present invention is concerned with a novel dental implant 50 and a two-piece abutment assembly 52 which is assembled to the dental implant, and a process for preparing a tooth prosthesis 54 which, ultimately, is fixed to the abutment assembly 52.

With reference to FIGS. 1–5, the dental implant 50 comprises an elongated tubular body 56 which is receivable within a bore 58 provided in the jawbone 60 of the patient. The tubular body 56 is provided with internal threads 62 which are adapted to threadably receive a threaded shank portion 64 of the abutment assembly 52. The tubular body 56 includes a skirt portion 66 radially movable from a first retracted position (shown in FIGS. 2 and 3) to a second expanded position (shown in FIG. 1). To move the skirt portion 66 into the second expanded position, there is provided expander means shown in the drawings as comprising an expansion nut 68 and a draw screw 70. As shown in FIG. 3, the tubular body 56 includes an internal shoulder 72 on which a slotted head 74 of the draw screw 70 rests. A threaded shank portion 76 of the draw screw 70 extends below the shoulder 72 generally to a lower end of the tubular body 56 whereat the expansion nut 68 is threaded onto the threaded shank 76. The expansion nut 68 includes a frustoconically-shaped skirt-engaging side wall which is adapted to engage inwardly sloping or inclined side walls 80 provided on the skirt portion 66 of the tubular body 56.

Figure 5:
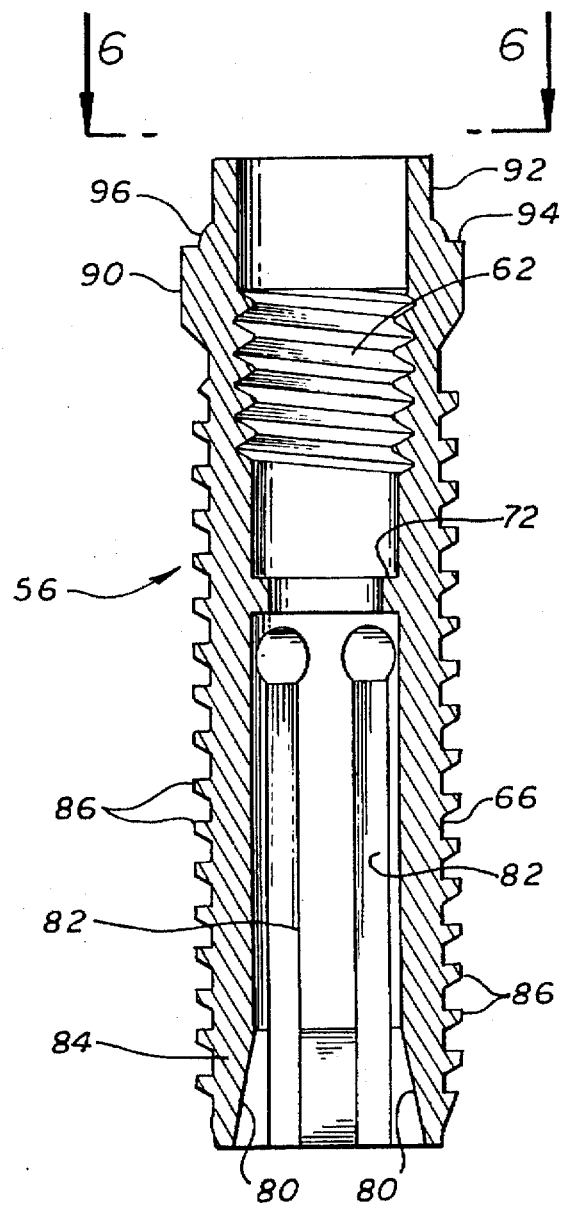
FIG. 5 is an elevational sectional view of the tubular body portion of the dental implant illustrated in FIGS. 2 and 3.
Figure 7:
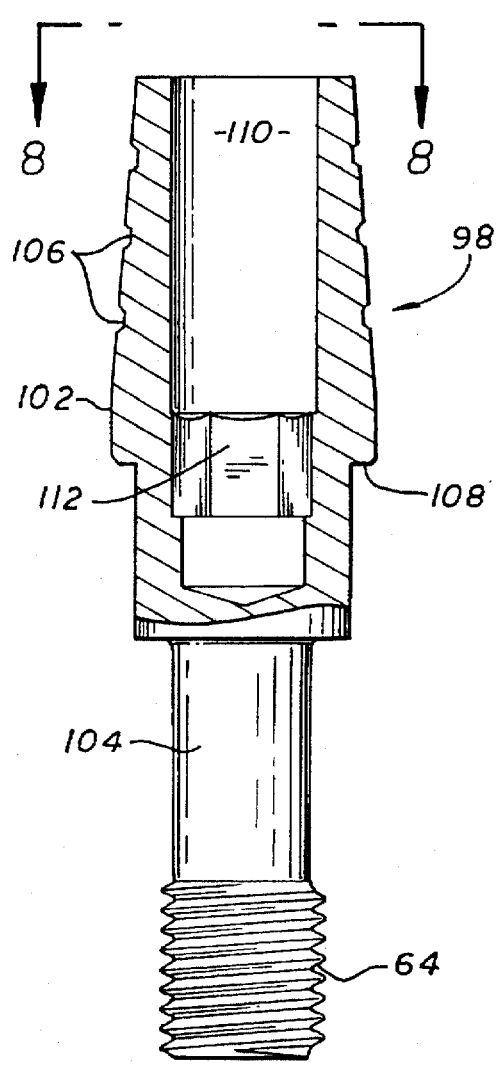
FIG. 7 is an elevational and partly sectional view of an abutment screw illustrated in FIGS. 2 and 3 forming a portion of the abutment assembly.
Figure 10:
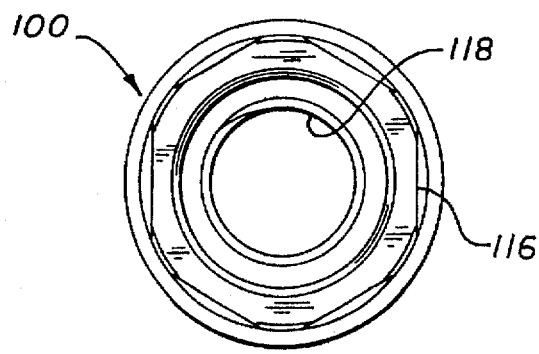
FIG. 10 is a top plan view of the abutment collar taken generally along the line 10—10 of FIG. 9.
Figure 9:
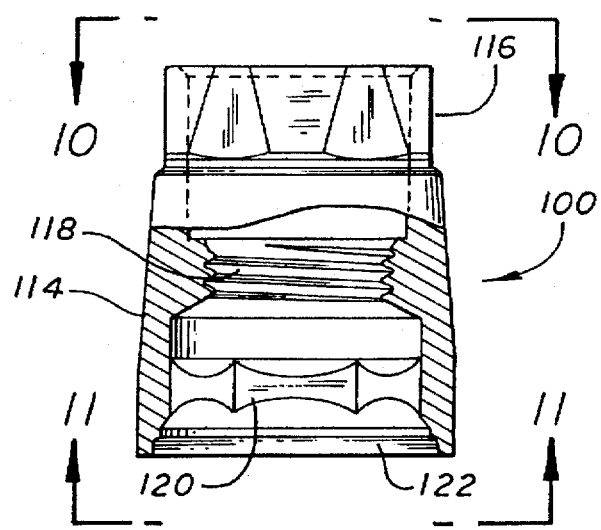
FIG. 9 is an elevational and partially sectional view of an abutment collar illustrated in FIGS. 2 and 3 forming a portion of the abutment assembly.
Figure 8:
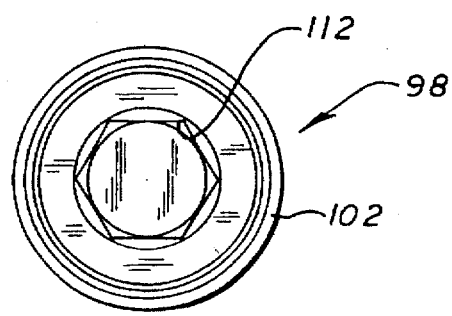
FIG. 8 is a top plan view of the abutment screw taken generally along the line 8—8 of FIG. 7.
Figure 11:
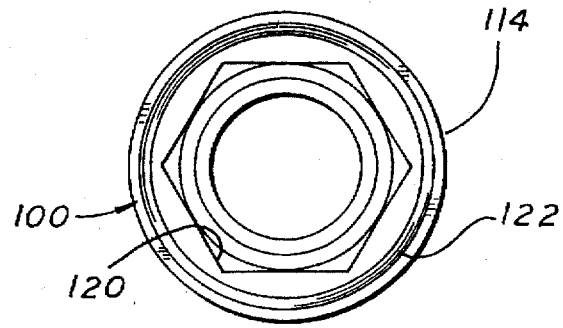
FIG. 11 is a bottom plan view of the abutment collar taken generally along the line 11—11 of FIG. 9.

As best shown in FIGS. 2 and 5, the skirt portion 66 of the tubular body 56 is provided with four circumferentially spaced elongated slits 82 which define four, separately-movable bone anchor segments 84 each having bone penetrating means provided in the form of a series of longitudinally spaced, blade-like bone penetrating protuberances 86. As the expansion nut 68 is drawn into the tubular body 56, the bone anchor segments 84 will be expanded outwardly so that penetrating protuberances 86 slice into the bone in a manner to securely lock the tubular body 56 within the bore 58. As the expansion nut 68 is being drawn into the tubular body 56, tabs 88 which extend outwardly from an upper portion of the expansion nut 68 travel upwardly through the elongated slits 82 to prevent rotation of the expansion nut 68 relative to the tubular body 56.

Figure 26:
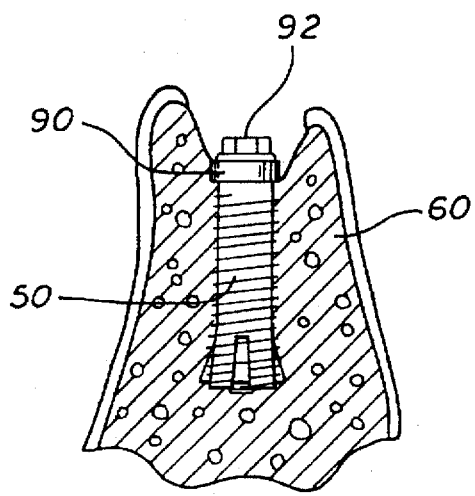

When the dental implant 50 is properly positioned within the jawbone 60 of the patient as illustrated in FIG. 26, an upper portion of the dental implant extends upwardly from the jawbone. This portion includes a cylindrical ring 90 having a diameter generally slightly larger than the diameter of the bore 58, and an uppermost, exteriorly hexagonal portion 92. The cylindrical ring 90 includes a generally planar upper shoulder 94, and a bevel 96 provides a transition between the upper shoulder 94 and adjacent surfaces of the upper hex 92.

Prior to placing the dental implant 50 within the jawbone 60 of a patient, the jawbone is first drilled to provide a bore 58 of a selected diameter, preferably slightly less than the diameter of the cylindrical ring 90. The dental implant 50 is prepared by simply placing the draw screw 70 within the tubular body 56 so that a slotted head 74 rests against the internal shoulder 72. The expansion nut 68 is threaded onto the bottom end of the threaded shank 76 just enough to ensure that the tabs 88 of the expansion nut 68 will be properly aligned with the elongated slits 82. This assembly of the tubular body 56, the draw screw 70 and the expansion nut 68 is then placed within the bore 58. A screwdriver may be inserted through the upper end of the tubular body 56 to turn the draw screw 70 for the purpose of drawing the expansion nut 68 upwardly into the tubular body 56. If necessary, a wrench may be utilized to engage the upper hex 92 to prevent rotation of the tubular body 56. The tabs 88 ensure that the expansion nut 68 does not rotate relative to the tubular body 56. As the expansion nut 68 is drawn into the tubular body 56, the bone anchor segments 84 expand outwardly so that the penetrating protuberances 86 slice into the bone in a manner to securely lock the tubular body 56 within the bore 58.

The abutment assembly 52 comprises two primary components, namely an abutment screw 98 and an abutment collar 100. The abutment screw 98 includes a head 102 and a shaft 104 that extends from the head 102 to the threaded shank 64. The head 102 has a frusto-conical outer surface with a plurality of circumferentially extending grooves 106 which assist in chair-side modification of the shape of the abutment assembly. The head 102 further includes a shoulder 108 which defines a transition area between the outer frusto-conical surface of the head and a generally cylindrical outer surface thereof which is positioned within the abutment collar 100. A longitudinal cavity 110 is provided within the head, and an internal hex surface 112 is formed within the cavity 110. The internal hex surface 112 facilitates turning of the abutment screw utilizing a suitable tool, to tighten the threaded shank 64 into the internal threads 62 of the tubular body 56 of the dental implant 50.

The abutment collar 100 includes a main body portion 114 which is configured to rest upon the upper shoulder 94 of the cylindrical ring 90 of the tubular body 56, and an upper collar 116 which has an exteriorly hexed surface. A central cavity extending longitudinally through the abutment collar 100 includes a threaded section 118 through which the threaded shank 64 of the abutment screw 98 passes, and an inner hexed surface 120 which is configured to mate with the upper hex 92 of the tubular body 56. Further, immediately adjacent to the inner hexed surface 120, the abutment collar 100 is provided an inner bevel 122 which is configured to mate with the bevel 96 adjacent to the upper shoulder 94.

It will be appreciated that the abutment assembly 52 differs from prior art structures in that the assembly has been separated into two different components, the abutment screw 98 and the abutment collar 100. In use, the abutment collar is placed over the cylindrical ring 90 of the tubular body 56 so that the inner hexed surface 120 mates with the upper hex 92, and a lower edge of the main body portion 114 rests upon the upper shoulder 94. This arrangement prevents rotation of the abutment collar 100 relative to the dental implant 50. The facing bevels 96 and 122 serve to ensure proper longitudinal alignment between the abutment collar 100 and the tubular body 56. The abutment screw 98 is threaded through the abutment collar 100 into the dental implant 50 until both the abutment screw 98 and abutment collar 100 are secured firmly in place to the implant 50. This particular arrangement ensures that the restoration or dental prosthesis which is attached to the abutment assembly 52 attaches to both components 98 and 100, thereby preventing relative rotation therebetween. In prior art abutments, a screw is typically passed into the open interior of the abutment to hold the abutment in place. This screw can come loose, since no part of the restoration fits directly to the screw.

Preferably the exterior surfaces of the abutment collar 100 are plated with titanium nitride to give the abutment collar 100 a gold color. This is desirable primarily for aesthetic reasons. In some cases, depending on the nature of the patient's gums, a silver abutment collar would be visible. The gold color of the abutment collar plated with titanium nitride minimizes shine through by providing the abutment collar a more natural color.

As illustrated in FIGS. 2 and 3, an elastomeric ball 124 is disposed between the end of the threaded shank 64 and the top of the slotted head 74 of the draw screw 70. This elastomeric ball, preferably of a silicone elastomeric material, is simply placed over the slotted head 74 prior to tightening the abutment screw 98 in place. As the threaded shank 64 is tightened into the internal threads 62 of the tubular body 56, the ball 124 is compressed. This serves to apply a force to both the draw screw 70 and the abutment screw 98, thereby resisting rotation of these components relative to the tubular body 56. A spring would be an equivalent structure.

FIGS. 12–14 illustrate a waxing sleeve 126. The function of the waxing sleeve will be fully described below in connection with the process steps illustrated in FIGS. 42–45. The waxing sleeve 126 is preferably manufactured of a clear plastic material that may be burned-off with a wax-up of a dental crown to be manufactured utilizing standard casting procedures. The waxing sleeve 126 is generally cylindrical having an open upper end 128 and an open lower end 130. A plurality of circumferential rings 132 are provided to facilitate handling of the waxing sleeve 126. An inner hexed surface 134 is provided within an internal cavity 136, and is configured to mate with a like-shaped upper collar 138 of an implant analog 140 (shown in FIGS. 23–25). The upper collar 138 of the implant analog 140 corresponds in shape to the upper collar 116 of the abutment collar 100. Adjacent the inner hexed surface 134, the internal cavity 136 includes an inner shoulder 142 which is configured to engage an upper end of the upper collar 138 of the implant analog 140.

FIGS. 15–17 illustrate a treatment crown sleeve 144. The treatment crown sleeve 144 is typically manufactured of the same hardened metals comprising the abutment assembly 52 and the tubular body 56, and comprises a generally tubular main body 146. A plurality of circumferentially extending rings 148 are provided to facilitate handling of the treatment crown sleeve 144, and further to facilitate bonding of composite materials thereto. Use of the treatment crown sleeve 144 will be further described below in connection with the process steps illustrated in FIGS. 35 and 36.

The inner configuration of the treatment crown sleeve 144 is identical to the inner configuration of the lower portion of the waxing sleeve 126. In this regard, the treatment crown sleeve 144 includes an inner hexed surface 150 having a configuration designed to mate precisely with the outer hexed surface of the upper collar 116 of the abutment collar 100. Further, an inner shoulder 152 is provided adjacent to the inner hexed surface 150 to provide an inner seating surface for the treatment crown sleeve 144 on an upper surface of the upper collar 116. Like the abutment collar 100, the treatment crown sleeve 144 is preferably plated with a titanium nitride material to give it a gold color for the same reasons discussed above.

FIG. 18 illustrates a transfer sleeve 154. The function of the transfer sleeve will be described fully below in connection with process steps illustrated in FIGS. 28–30 and 38–40. The top and bottom plan views of the transfer sleeve 154 are identical to the top and bottom plan views of the treatment crown sleeve 144, as shown in FIGS. 16 and 17.

The transfer sleeve 154 is, essentially, a shortened version of the treatment crown sleeve 144. It includes a tubular main body 156 with a plurality of circumferentially extending outer rings 158. An inner hexed surface 160 is provided for matingly engaging the upper collar 116 of the abutment collar 100. Further, an inner shoulder 162 is provided to rest directly upon an upper end of the upper collar 116.

FIGS. 19–22 illustrate an impression sleeve 164. The function of the impression sleeve 164 will be described below in connection with the process steps illustrated in FIGS. 31–34 and 37. The impression sleeve is preferably formed of a clear plastic material and comprises a generally tubular body 166 having four apertures 168 therethrough. The apertures facilitate displacement of composite material when an impression is made as described below. The impression sleeve 164 is similar in construction to the waxing sleeve 126, and includes an open upper end 170, an open lower end 172 and an inner cavity 174. The inner cavity 174 is provided an inner hexed surface 176 which is configured to mate precisely with both the upper collar 116 of the abutment collar 100 and the upper collar 138 of the implant analog 140. An inner shoulder 178 is provided adjacent to the inner hexed surface 176 to engage an upper end of the upper collars 116 and 138.

It should be understood that the inner configuration of the inner hexed surfaces and inner shoulders of the waxing sleeve 126, the treatment crown sleeve 144, the transfer sleeve 154 and the impression sleeve 164 are identical. It is intended that each of these components fit in precisely the same way upon the identical upper collars 116 and 138 of the abutment collar 100 and the implant analog 140.

FIGS. 23–25 illustrate the implant analog 140. The function of the implant analog 140 will be described below in connection with the process steps illustrated in FIGS. 34 and 37–45. The implant analog 140 comprises a generally tubular body which has three circumferentially extending rings 180. The lower portion of the implant analog 140 is configured simply for ease in handling and for securement within a stone mold 182 (see FIG. 41). The upper portion 184 of the implant analog 140 duplicates the exterior configuration of the abutment collar 100, including a main body portion 186 (which duplicates the main body portion 114), and the upper collar 138 (which duplicates the upper collar 116).

Figure 28:
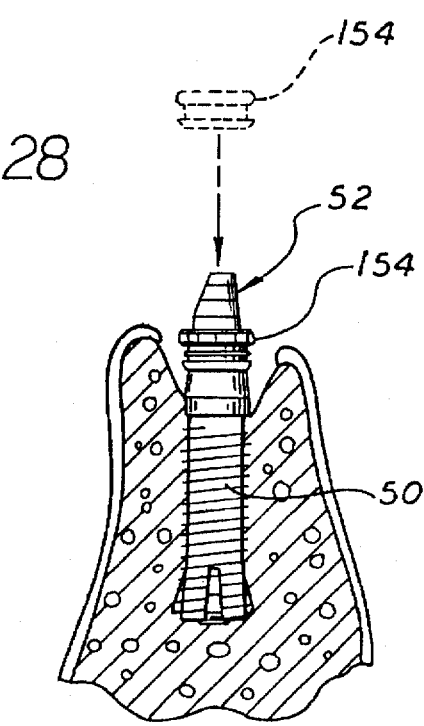
Figure 27:
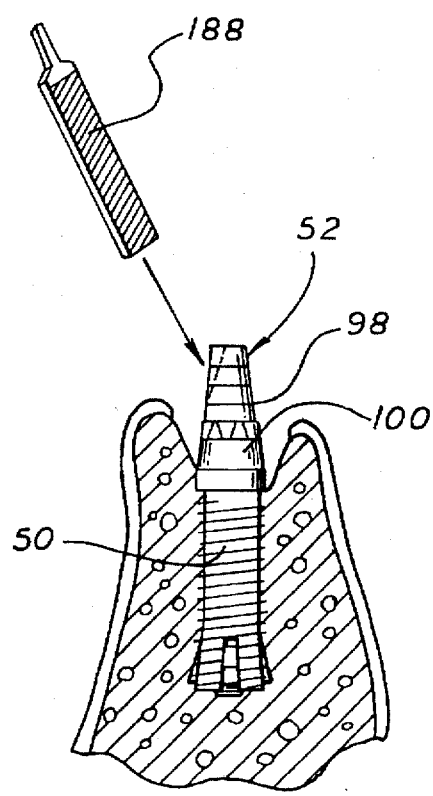

Turning now to FIGS. 26–46, the process for preparing a tooth prosthesis in accordance with the present invention will now be described. First, the dental implant 50 is positioned within the bore 58 in the jawbone 60 as described above and illustrated in FIG. 26. Next, the abutment assembly 52 secured to the dental implant 50 as described above. As schematically illustrated in FIG. 27, a file 188 or another suitable tool many be utilized to shape the head 102 of the abutment screw 98. As shown in FIG. 28, the transfer sleeve 154 is then placed over the abutment assembly 52 so that the inner shoulder 162 rests upon the upper edge of the abutment collar 100 and so that the inner hexed surface 160 engages the hexed outer surface of the upper collar 116.

Figure 29:
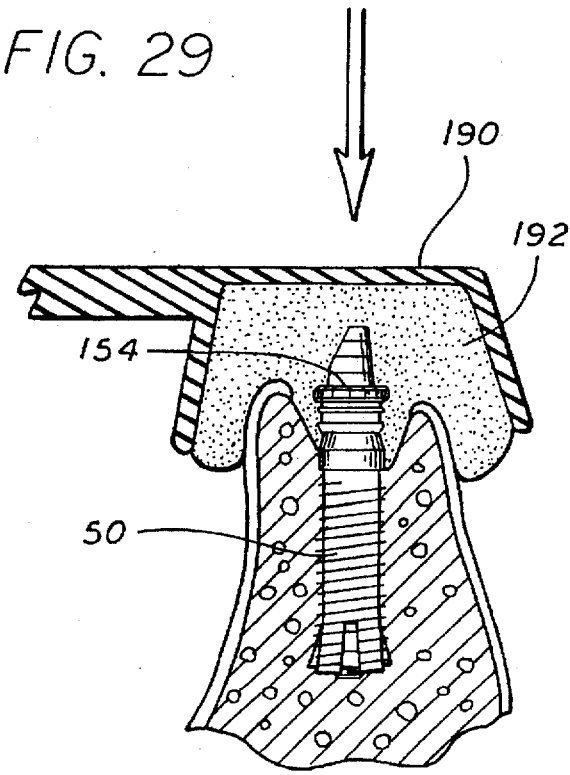
Figure 30:
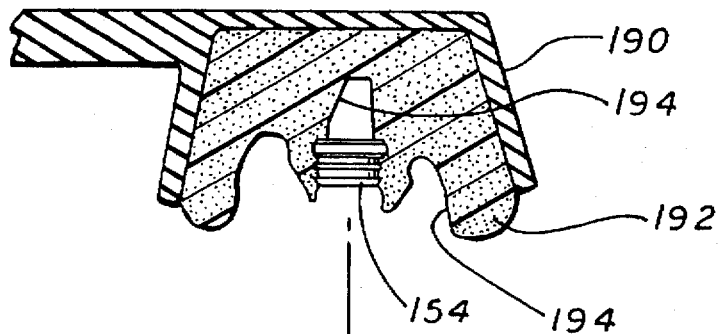

As illustrated in FIGS. 29 and 30, a suitable holder 190 is filled with impression material 192, and an impression is taken of the mouth. As the impression material 192 is removed from the mouth, the transfer sleeve 154 is also removed from the abutment assembly 52 adjacent to the impression 194 of the customized abutment.

Figure 31:
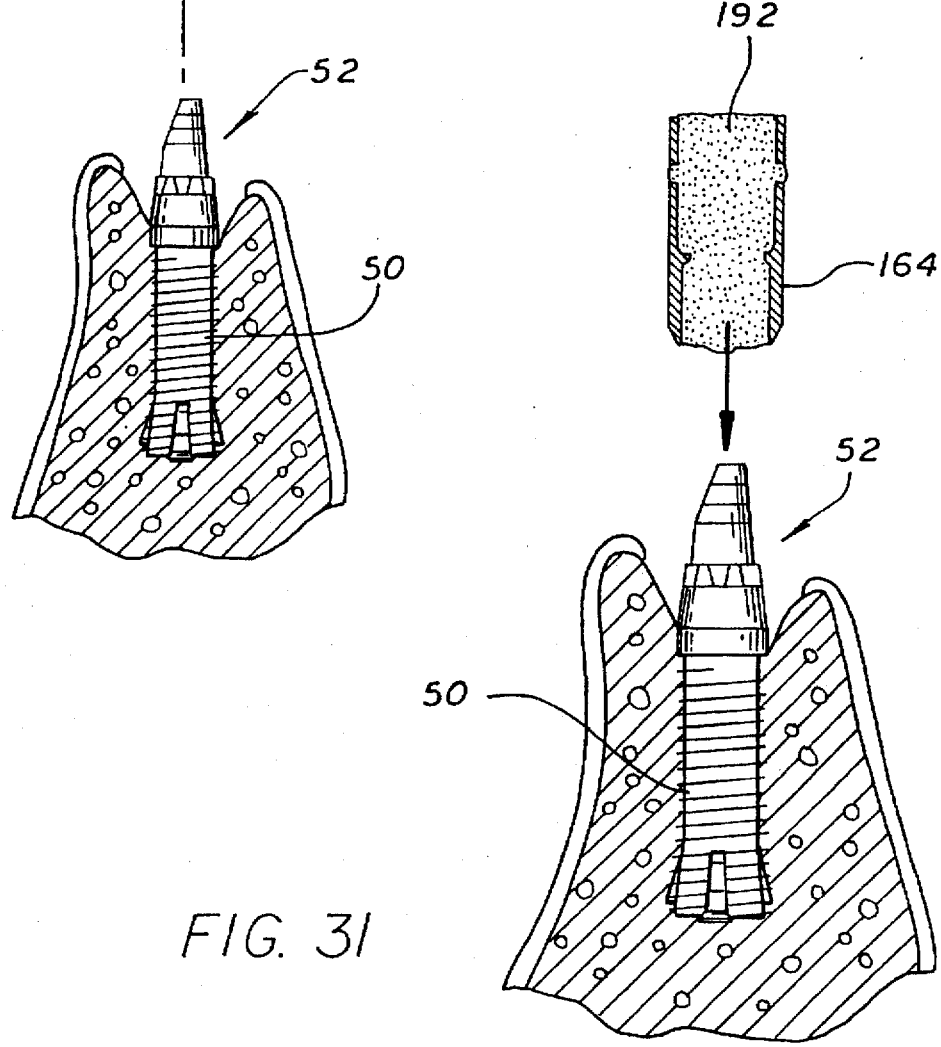

With reference to FIGS. 31–34, next the impression sleeve 164 is filled with impression material 192 and placed over the customized abutment assembly 52 so that the inner hexed surface 176 of the impression sleeve engages the upper collar 116 of the abutment collar 100 (FIG. 31). The impression sleeve 164 is then removed from the mouth (FIG. 32), filled with a composite or a die stone material 196 (FIG. 33) and then fully seated onto the upper portion 184 of the implant analog 140 (FIG. 34). This procedure will duplicate the external configuration of the modified abutment assembly 52 with a composite stone mold affixed to the upper end 184 of the implant analog 140.

Figures 35, 36:
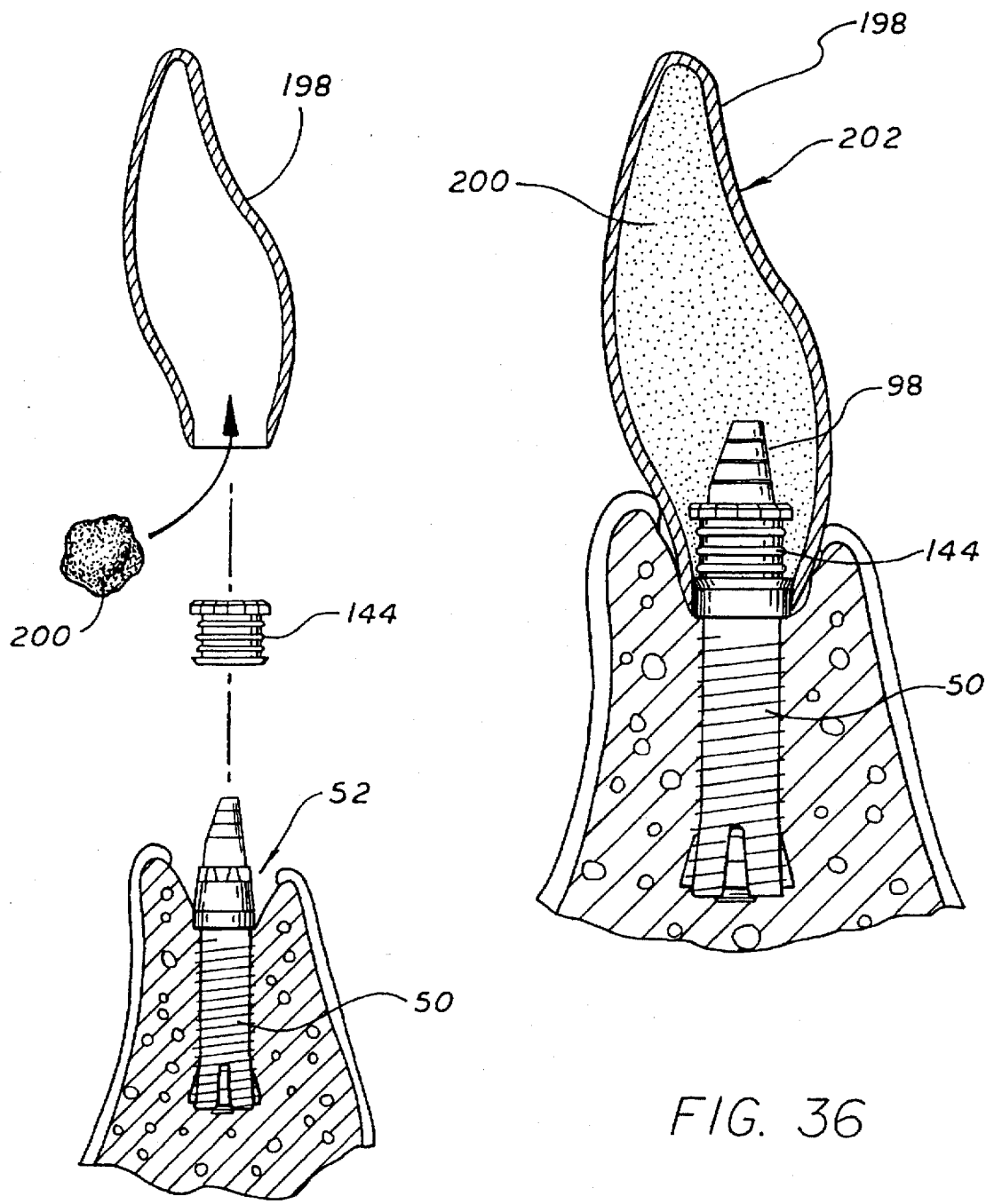

With reference to FIGS. 35 and 36, immediate provisionalization can be accomplished following dental implant 50 placement when the supporting bone is of good quality (type I, II and frequently III) and the aesthetic and/or psychological needs of the patient dictate.

A custom acrylic resin crown or fixed prosthesis can be made beforehand from waxed-corrected casts of the patient's dentition. For single units, a hollowed-out, properly selected acrylic resin denture tooth 198 may be used as an alternative. The treatment crown sleeve 144 is utilized in connection with this immediate provisionalization. The denture tooth 198 is filled with a composite material, and the treatment crown sleeve 144 is placed over the modified abutment assembly 152 so that the inner hexed surface 150 fully engages the upper collar 116 of the abutment collar 100. A cold cure acrylic resin is placed within the denture tooth (provisional restoration). When the acrylic resin 200 begins to set, the provisional 198 is placed over the customized abutment assembly 52 and the treatment crown sleeve 144, making certain the align the provisional 198 with the adjacent teeth. After the acrylic resin 200 has set, the provisional denture tooth 202 is removed from the mouth. The provisional tooth now incorporates the treatment crown sleeve 144. The treatment crown sleeve 144 provides internal titanium strength, better frictional retention and a precision fit margin for the provisional tooth 202. The provisional tooth 202 may then be contoured, polished and adjusted as necessary to establish a natural anatomic profile. The provisional tooth 202 may then be reattached over the modified abutment assembly 52 until a permanent crown is prepared as discussed below.

Returning to the implant analog 140 which has received the impression sleeve 164 filled with the die stone composite material 196, once the composite is set, the impression sleeve is removed (FIG. 37). This results in a custom analog 204 which is the exact duplicate of the modified abutment assembly 52. The custom analog 204 is placed into the original impression 194 to fit inside the transfer sleeve 154 (FIG. 38). A cast 206 is utilized and stone is poured within the cast over the exposed portion of the implant analog 140 (FIG. 39). Once the stone 208 has set-up, the holder 190 and impression material 192 containing the transfer sleeve 154 are removed from the custom analog 204, and the cast 206 is removed from the stone 208 (FIG. 40). The result is a stone mold 182 which is an exact model of the mouth (FIG. 41).

Figure 45:
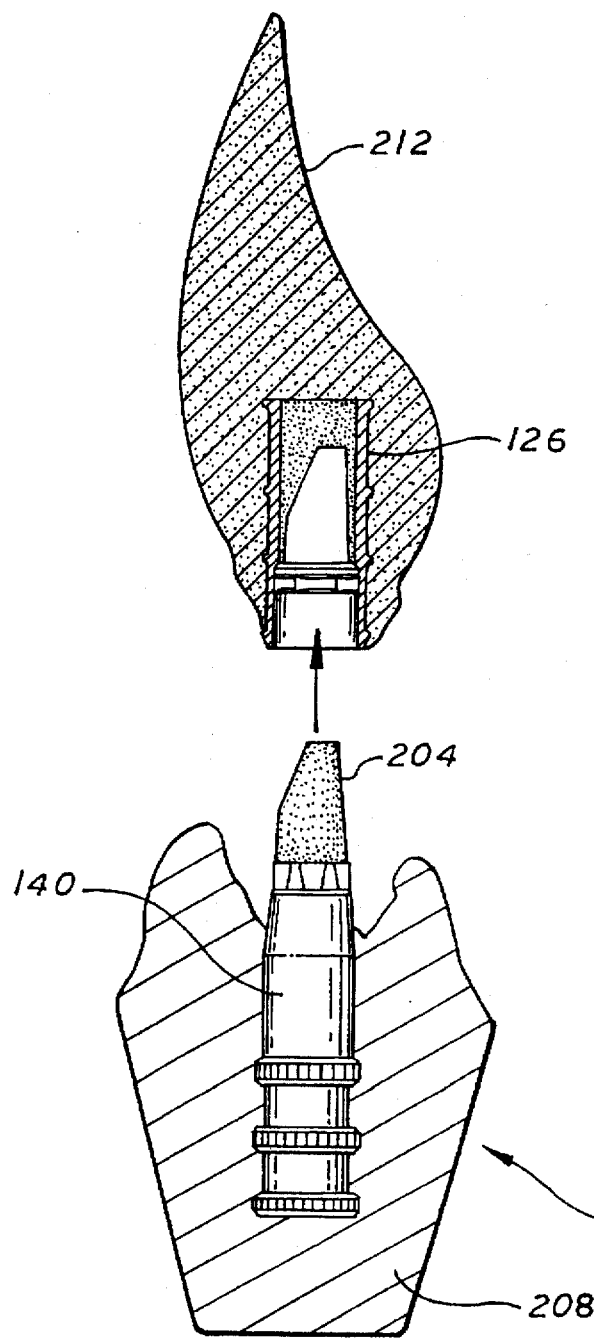
Figure 46:
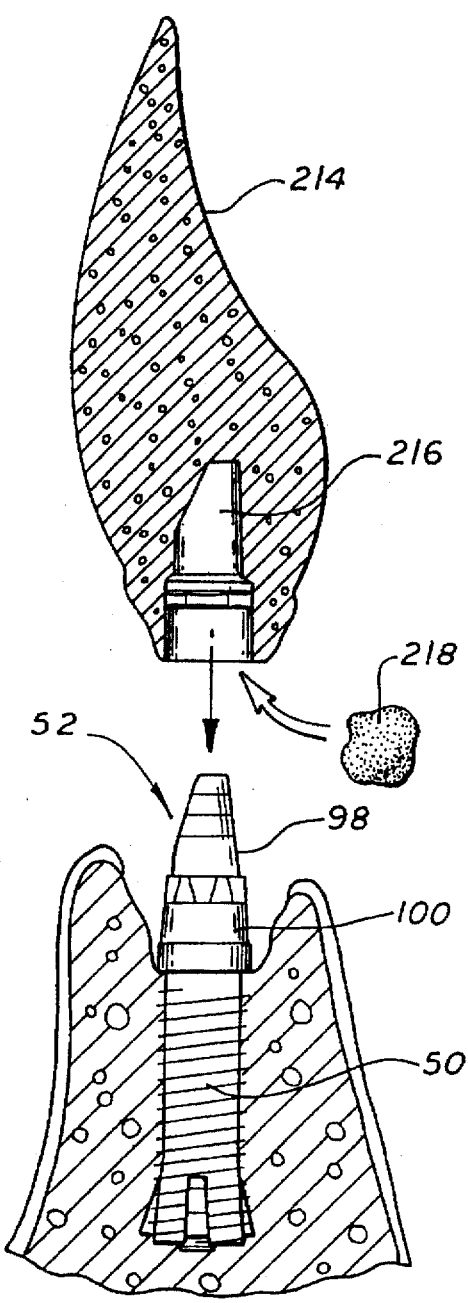

Next, the waxing sleeve 126 is placed over the custom analog 204 (FIG. 42) so that the inner hexed surface 134 fully engages the upper collar 138 of the implant analog 140. The waxing sleeve 126 is then filled with wax 210 (FIG. 43), and then a wax-up 212 in the shape of a tooth is then formed in the standard fashion (FIG. 44). The wax-up 212, including the waxing sleeve 126 which bears an impression of the custom analog 204, is then removed from the custom analog (FIG. 45) and placed in investment stone for purposes of forming a crown in a manner well known to those of ordinary skill in the art (FIG. 45). During the manufacture of a crown 214 corresponding in shape to the wax-up 212, the wax 210 and the waxing sleeve 126 are burned off. The resulting crown 214 has an internal cavity 216 exactly configured to match the custom analog 204 and the modified abutment assembly 52. Finally, an adhesive 218 is placed within the internal cavity 216, and the crown 214 is secured to the customized abutment assembly 52 (FIG. 46). The resulting structure is illustrated in FIG. 1.

From the foregoing it is to be appreciated that the present invention provides a novel dental implant assembly that includes a two-piece abutment which, when a crown 214 is secured thereto, is incapable of rotation relative to the underlying dental implant 50. Additionally, the process of the present invention permits conditions within the mouth, including the configuration of the dental implant assembly, to be exactly replicated in a stone mold 182. This permits a laboratory technician to accurately manufacture a crown 214 that will properly fit when placed within the patient's mouth.

Although a particular embodiment of the invention has been described in detail for purposes of illustration, various modifications may be made without departing from the spirit and scope of the invention. Accordingly, the invention is not to be limited, except as by the appended claims.

I claim:

1. A dental assembly, comprising:
    an implant assembly including a skirt receivable within a bore provided in a jawbone of a patient, and supporting means extending from the skirt and adapted to extend outwardly from the bore, the supporting means including at least one radially outwardly facing planar surface, and the skirt being radially movable within the bore from a first retracted position to a second expanded position and including an internal shoulder, the implant assembly further including a draw screw having a head that rests on the internal shoulder and a threaded shank which extends to an end of the skirt, and an expansion nut having a frustoconically-shaped skirt-engaging side wall and an inner threaded cavity into which the shank of the draw screw is threaded, whereby rotation of the draw screw through the inner cavity of the expansion nut causes radial movement of the skirt from the first retracted position to the second expanded position;
    an abutment collar having a central cavity defining at least one radially inwardly facing planar surface which, when the abutment collar is positioned over at least a portion of the supporting means, the radially facing surfaces of the supporting means and the abutment collar interfit to prevent rotation of the abutment collar relative to the implant assembly; and
    an abutment screw having a head positionable in abutting relation to the abutment collar opposite the implant assembly, and a shank that extends from the head through the central cavity of the abutment collar for connection to the implant assembly.

2. The dental assembly of claim 1, wherein the shank of the abutment screw is threaded.

3. The dental assembly of claim 1, wherein the abutment collar includes a main body positionable over at least a portion of the supporting means, and a collar opposite the implant assembly relative to the main body, which collar includes at least one radially outwardly facing planar surface.

4. The dental assembly of claim 3, wherein the collar of the abutment collar includes a plurality of radially outwardly facing planar surfaces to form a hexed outer periphery.

5. The dental assembly of claim 3, wherein the at least one radially inwardly facing planar surface of the abutment collar includes a plurality of such surfaces forming an inner hexed surface, and wherein the abutment collar further includes an internal threaded section through which the abutment screw shank extends.

6. The dental assembly of claim 3, wherein the central cavity of the abutment collar defines an inner bevel positioned adjacent to the supporting means and configured to engage a complimentary outer bevel provided on the implant assembly.

7. The dental assembly of claim 1, wherein the skirt comprises at least two anchor segments moveable from the first retracted position to the second expanded position, wherein the skirt includes an inclined internal surface, and wherein the expansion nut comprises a skirt engaging portion having an inclined external surface moveable into engagement with the inclined internal surface of the skirt upon rotation of the draw screw through the inner cavity of the expansion nut, wherein the anchor segments include bone penetrating means for penetrating the bone of the patient upon movement of the segments into the second expanded position.

8. The dental assembly of claim 7, wherein the skirt includes a plurality of circumferentially spaced, longitudinally extending slits which separate the anchor segments, and wherein the expansion nut includes a plurality of tabs configured for alignment with the longitudinally extending slits.

9. The dental assembly of claim 1, wherein the draw screw is positioned entirely within the skirt and is accessible through the supporting means.

10. The dental assembly of claim 1, wherein the supporting means includes a ring having a diameter larger than the bore wherein the ring provides a shoulder facing away from the bore, an upper hexed portion extending away from the ring and presenting a plurality of radially outwardly facing planar surfaces, and a bevel adjacent to the shoulder and surrounding the upper hexed portion.

11. The dental assembly of claim 1, wherein the abutment collar has a gold color.

12. A dental assembly, comprising:

an elongated hollow body including a skirt receivable within a bore provided in a jawbone of a patient, and means extending from the skirt and adapted to extend outwardly from the bore for supporting a prosthetic component, wherein the skirt is radially movable within the bore from a first retracted position to a second expanded position and includes an internal shoulder, and wherein the supporting means includes at least one radially outwardly facing planar surface that may be engaged by the prosthetic component to prevent relative rotation therebetween;

a draw screw having a head that rests on the internal shoulder and a threaded shank connected to the head and which extends to an end of the skirt; and an expansion nut having a frustoconically-shaped skirt-engaging side wall and an inner threaded cavity into which the shank of the draw screw is threaded, whereby rotation of the draw screw through the inner cavity of the expansion nut causes radial movement of the skirt from the first retracted position to the second expanded position.

13. The dental assembly of the claim 12, wherein the skirt includes an inclined internal surface, and wherein the expansion nut comprises a skirt engaging portion having an inclined external surface moveable into engagement with the inclined internal surface of the skirt upon rotation of the draw screw through the inner cavity of the expansion nut.

14. The dental assembly of claim 12, wherein the skirt comprises at least two anchor segments moveable from the first retracted position to the second expanded position.

15. The dental assembly of claim 14, wherein the anchor segments include bone penetrating means for penetrating the bone of the patient upon movement of the segments into the second expanded position.

16. The dental assembly of claim 14, wherein the skirt includes a plurality of circumferentially spaced, longitudinally extending slits which separate the anchor segments.

17. The dental assembly of claim 16, wherein the expansion nut includes a plurality of tabs configured for alignment with the longitudinally extending slits.

18. The dental assembly of claim 12, wherein the draw screw is positioned entirely within the skirt and is accessible through the supporting means.

19. The dental assembly of claim 12, wherein the supporting means includes a ring having a diameter larger than the bore, wherein the ring provides a shoulder facing away from the bore, and an upper hexed portion extending away from the ring and presenting a plurality of radially outwardly facing planar surfaces.

20. The dental assembly of claim 19, including a bevel adjacent to the shoulder and surrounding the upper hexed portion.

21. The dental assembly of claim 12, wherein the prosthetic component includes a two-piece abutment assembly having an abutment collar that engages the at least one planar surface of the supporting means, and an abutment screw having a head positioned adjacent to the abutment collar and a shank threadably received within the hollow body.

22. The dental assembly of claim 21, including an elastomeric ball compressed between the abutment screw shank and the draw screw head.

23. The dental assembly of claim 21, wherein the abutment collar is plated with a gold-colored material.

24. The dental assembly of claim 21, wherein the abutment collar includes at least one radially inwardly facing planar surface which, when the abutment collar is positioned over at least a portion of the supporting means, the radially facing surfaces of the supporting means and the abutment collar interfit to prevent rotation of the abutment collar relative to the hollow body.

25. The dental assembly of claim 24, wherein the abutment collar includes a main body positionable over at least a portion of the supporting means, and a collar opposite the implant assembly relative to the main body, which collar includes at least one radially outwardly facing planar surface.

26. The dental assembly of claim 25, wherein the collar of the abutment collar includes a plurality of radially outwardly facing planar surfaces to form a hexed outer periphery.

27. The dental assembly of claim 26, wherein the at least one radially inwardly facing planar surface of the abutment collar includes a plurality of such surfaces forming an inner hexed surface, and wherein the abutment collar further includes an internal threaded section through which the abutment screw shank extends, wherein the abutment collar includes an inner bevel configured to engage a complimentary outer bevel provided on the implant assembly.

28. The dental assembly of claim 21, wherein the abutment screw includes a head positionable in abutting relation to the abutment collar opposite the hollow body, and wherein the shank is extendable through the abutment collar for connection to the hollow body.

29. The dental assembly of claim 28, wherein the shank is threaded at an end thereof.

30. A dental assembly comprising:

a dental implant including a skirt receivable within a bore provided in a jawbone of a patient, the skirt being radially movable within the bore from a first retracted position to a second expanded position, the dental implant further including an expansion nut having a frustoconically-shaped skirt-engaging side wall, and means for pulling the expansion nut into the skirt to cause radial movement of the skirt from the first retracted position to the second expanded position;

an abutment collar including a main body portion positionable over the dental implant, a collar portion extending away from the dental implant relative to the main body portion, and a central cavity therethrough, the main body portion including means engagable with the dental implant for preventing relative rotation of the abutment collar relative to the dental implant; and an abutment screw having a head positionable in abutting relation to the abutment collar opposite the dental implant, and a shank that extends from the head through the central cavity of the abutment collar for connection to the dental implant.

31. The dental assembly of claim 30, wherein the rotation preventing means of the abutment collar comprises at least one radially inwardly facing planar surface.

32. The dental collar of claim 31, wherein the collar portion of the abutment collar includes a plurality of radially outwardly facing planar surfaces to provide a hexed outer periphery.

33. The dental assembly of claim 31, wherein the central cavity of the abutment collar defines an internal bevel generally adjacent to the at least one radially inwardly facing planar surface and which is configured to mate with a corresponding bevel provided on the dental implant.

34. The dental assembly of claim 30, wherein the shank of the abutment screw is threaded for threaded reception into threads provided within the dental implant.

35. The dental assembly of claim 30, wherein the head of the abutment screw includes a longitudinally extending internal cavity.

36. The dental assembly of claim 35, including an internal hexed surface within the internal cavity.

37. The dental assembly of claim 30, wherein the skirt of the dental implant includes an internal shoulder, and wherein the pulling means comprises a draw screw having a head that rests on the internal shoulder and a threaded shank which extends to an end of the skirt, the expansion nut having an inner threaded cavity into which the shank of the draw screw is threaded, whereby rotation of the draw screw through the inner cavity of the expansion nut causes the radial movement of the skirt from the first retracted position to the second expanded position.

* * * * *